(12) United States Patent
Manna

(10) Patent No.: US 8,162,858 B2
(45) Date of Patent: Apr. 24, 2012

(54) ULTRASONIC MEDICAL TREATMENT DEVICE WITH VARIABLE FOCAL ZONE

(75) Inventor: Ronald R. Manna, Valley Stream, NY (US)

(73) Assignee: US Hifu, LLC, Charlotte, NC (US)

( * ) Notice: Subject to any disclaimer, the term of this patent is extended or adjusted under 35 U.S.C. 154(b) by 1466 days.

(21) Appl. No.: 11/296,554

(22) Filed: Dec. 7, 2005

(65) Prior Publication Data

US 2006/0184072 A1 Aug. 17, 2006

Related U.S. Application Data

(60) Provisional application No. 60/635,530, filed on Dec. 13, 2004.

(51) Int. Cl.
*A61H 1/00* (2006.01)
(52) U.S. Cl. .................................. 601/2; 601/3; 601/46
(58) Field of Classification Search .................. 600/437, 600/407; 601/2
See application file for complete search history.

(56) References Cited

U.S. PATENT DOCUMENTS

| 4,276,779 A * | 7/1981 | Davis, Jr. ........................ 73/626 |
| 4,957,099 A | 9/1990 | Hassler |
| 5,207,226 A * | 5/1993 | Bailin et al. ................... 600/454 |
| 6,546,803 B1 * | 4/2003 | Ptchelintsev et al. ........... 73/632 |
| 6,613,005 B1 * | 9/2003 | Friedman et al. ................. 601/2 |
| 6,719,694 B2 * | 4/2004 | Weng et al. .................... 600/439 |
| 2001/0031922 A1 | 10/2001 | Weng et al. |

* cited by examiner

*Primary Examiner* — Tse Chen
*Assistant Examiner* — Joel F Brutus
(74) *Attorney, Agent, or Firm* — Reed Smith LLP; William J. McNichol, Jr.

(57) ABSTRACT

An ultrasonic medical treatment device takes the form of an elongate probe having an elongate wave-generating concave surface with a longitudinal axis and ultrasonic electromechanical transducer elements for vibrating said concave surface to generate ultrasonic pressure waves focused along a linear locus extending parallel to said longitudinal axis. The probe may include a monolithic piezoelectric crystal element and electrode pairs provided along the unitary or monolithic element in a spaced array.

16 Claims, 5 Drawing Sheets

ULTRASONIC MEDICAL TREATMENT DEVICE WITH VARIABLE FOCAL ZONE

CROSS-REFERENCE TO RELATED APPLICATION

This application claims the benefit of U.S. Provisional Patent Application No. 60/635,530 filed Dec. 13, 2004.

FIELD OF THE INVENTION

This invention relates to a medical device and more specifically to an ultrasonic minimally or non-invasive tissue ablation instrument. Even more specifically, this invention relates to an ultrasonic medical treatment device with a variable and shaped focal zone. This invention also relates to an associated medical treatment method.

BACKGROUND OF THE INVENTION

In modern medicine, many forms of energy are used for their therapeutic effect. Radio-frequency electric current, microwave energy and cryogenically chilled probes are all used to ablate diseased tissue, such as cancer lesions in the body. These devices have significantly improved the treatment results over using scalpel and sutures alone.

Another form of energy that has come under consideration for use as a therapeutic agent is ultrasound waves or ultrasonic acoustic energy. Ultrasound has long been used for diagnostic procedures where the waves are generated and collected much the same way that sonar wave are. These ultrasound waves are of an energy level that has no therapeutic effects, meaning that the ultrasound waves do not change the tissue structure in any way. The frequency of such waves is generally in the 5 to 30 MHz range.

Another ultrasound device that has been employed for decades is the ultrasonic diathermy instrument. This instrument uses an ultrasonic transducer to generate ultrasound waves at a higher intensity level than the diagnostic units. The acoustic waves are transmitted into the body where they are attenuated and absorbed. This absorption of energy causes the tissue temperature to rise, thereby causing deep heating of tissue. This heating is not sufficient to cause cell death, but promotes healing by increasing blood flow to the region, the same as if heating compresses were used.

The acoustic waves in both the diagnostic and diathermy machines are collimated or non-focused. In the new field of ultrasonic therapy, acoustic waves are focused to a point within a patient's tissues. By concentrating this energy at a specific location, the energy density increases to the point that ablation or necrosis of the tissue occurs. Such therapy has been given the designation "High Intensity Focused Ultrasound" or "HIFU."

Many different forms of HIFU generators or transducers have been proposed over the years. All of these devices take the energy output of an entire crystal face and through either curvature of the crystal itself or by focusing acoustic lenses concentrate the energy at a single point. An ordinary magnifying glass is a simple analogy where light energy is focused to a point in space. The concentrated energy can then easily raise the temperature of paper to greater than the flammability point.

One device is currently being marketed in Europe and Asia primarily for treatment of prostate disease but has also been proven to be effective in ablating lesions within the liver and kidneys as well. In this design, the circumference of the crystal is shaped as part of a concave surface. Since the acoustic waves propagate in a direction perpendicular to the face of the vibrating crystal, the waves will propagate in a manner such that they will converge at the focal point of the concave surface, FIG. 1, assuming that the crystal is in contact with a medium which will allow acoustic wave transmission, such as water or body tissues. As the waves propagate to the focal point, the acoustic energy density, watts/cm$^2$, increases to a point at which the temperature of the tissue rises above the ablation point. In addition to thermal effects, cavitation and micro streaming of the liquids surrounding the cells has been identified as mechanisms of cell destruction. In any event, the cells are rendered unviable. The body will then remove the necrotic tissue with its normal cleansing mechanism.

In the embodiment described above, the focal zone is theoretically a point in space, but in actuality it will be a small three-dimensional volume. It has been described as having the shape of a rice kernel. In order to treat a larger volume, the transducer head must be manipulated by the physician to treat another location, move it again and so on until the operation is completed.

The several HIFU devices that have been used clinically share at least one attribute: the focal point is quite small in volume. In some cases, this is desirable since only a discrete volume of tissue needs to be treated or the treatment area is close to or contiguous with healthy or important structures such as bile ducts. However, in some cases, a much larger volume of tissue must be ablated, such an entire kidney lobe. When such a large volume needs to be ablated, the only possibility has been to treat a volume, then physically move transducer head to a different location and treat that volume, move the head and so on. This has increased the operation time and operator fatigue factor considerably. Conversely, if a transducer were constructed that provided a very large focal zone, the transducer would not be able to be used for smaller lesions or for discrete points around viable tissue or structures.

OBJECTS OF THE INVENTION

An object of the present invention is to provide an improved ultrasonic ablation device.

A more specific object of the present invention is to provide a HIFU transducer assembly or probe that provides not only a large focal zone or treatment volume but also allows the operator to significantly expand or contract that volume at will.

Another specific object of the present invention to provide a HIFU transducer that projects acoustic waves into the body so that the waves converge to a focal point that is adjustable in size and intensity by the operator.

These and other objects of the invention will be apparent from the drawings and descriptions herein. Although every object of the invention is believed to be attained by at least one embodiment of the invention, there is not necessarily any single embodiment that attains all of the objects of the invention.

SUMMARY OF THE INVENTION

An ultrasonic medical treatment device in accordance with the present invention comprises an elongate probe having an elongate wave-generating concave surface with a longitudinal axis and ultrasonic electromechanical transducer elements for vibrating said concave surface to generate ultrasonic pressure waves focused along a linear locus extending parallel to said longitudinal axis.

In one embodiment of the present invention, the probe includes a unitary or monolithic element typically made of a piezoelectric crystal material. The concave surface is a surface of the crystal element. The transducer elements may include electrode pairs provided along the unitary or monolithic element in a spaced array.

In another embodiment of the present invention, the probe includes a plurality of separate piezoelectric crystal elements disposed in a predetermined array. The separate crystal elements are typically provided with respective pairs of electrodes for vibrating the crystals to generate the ultrasonic pressure waves focused along the linear locus.

An ultrasonic medical treatment device in accordance with the present invention comprises a probe having a plurality of wave-generating elements each for focusing ultrasonic pressure waves at a respective locus of focal points extending in at least one dimension, the loci of focal points being different and spaced from each other. The wave-generating elements include ultrasonic electromechanical transducer elements for vibrating at least one surface to generate ultrasonic pressure waves focused along the respective loci. The transducer elements are independently energizable to focus ultrasonic waveform energy selectively along the different loci.

Preferably, the probe is elongate and has a longitudinal axis, while the loci of focal points are linear and extend parallel to the longitudinal axis. More particularly, the probe has an elongate wave-generating concave surface formed along the longitudinal axis.

In one particular embodiment of the invention, the probe includes a plurality of segments each having a respective wave-generating concave surface, the ultrasonic electromechanical transducer elements vibrating the respective wave-generating concave surfaces to generate ultrasonic pressure waves focused along respective linear loci extending parallel to the longitudinal axis. The loci are parallel to and spaced from one another, while the probe segments are spaced from one another in a direction transverse to the longitudinal axis. Where the probe has a plane of symmetry, the segments include pairs of segments, each such pair including members disposed on opposite sides of the plane. The transducer elements may be disposed in a stepped array.

In another particular embodiment of the present invention, the loci are collinear and the probe segments are disposed in a linear array extending parallel to the longitudinal axis. Adjacent segments are preferably joined to one another by resilient spacer elements, with different segments being independently energizable. Thus, the energization of different groups of transducers results in the focusing of ultrasound waveform energy along different focal loci.

In yet another embodiment of the invention, the probe includes a plurality of segments disposed in an arc relative to one another, each of the segments having a respective wave-generating surface. The ultrasonic electromechanical transducer elements serve to vibrate the respective wave-generating surfaces to generate ultrasonic pressure waves focused along respective linear loci extending parallel to the longitudinal axis of the probe and transversely spaced from one another. Where the probe has a plane of symmetry, the segments including pairs of segments, each such pair including members disposed on opposite sides of the plane.

Pursuant to another feature of the present invention, the probe includes an epoxy lens along an inner side and a backing along an outer side, the transducer elements being disposed between the epoxy lens and the backing.

The present invention further contemplates an ultrasonic medical treatment device comprising (a) an elongate probe having an elongate wave-generating concave surface with a longitudinal axis and (b) ultrasonic electromechanical transducer elements the serve to vibrate the concave surface to generate ultrasonic pressure waves focused along a linear locus extending parallel to the longitudinal axis.

The surface has a transverse cross-sectional shape preferably taken from the group consisting of circular, parabolic, and conical, the cross-sectional shape being taken in a plane oriented substantially perpendicularly to the locus and the longitudinal axis.

The probe may include a plurality of segments each having a respective wave-generating concave surface, the ultrasonic electromechanical transducer elements vibrating the respective wave-generating concave surfaces to generate ultrasonic pressure waves focused along respective linear loci extending parallel to the longitudinal axis. The segments may be spaced from one another in a direction transverse to the longitudinal axis or may be disposed in a linear array extending parallel to the longitudinal axis. In the latter case, the individual loci are collinear, while in the former case the different loci may be spaced from one another in the transverse direction. Adjacent segments may be joined to one another by resilient spacer elements, the transducer elements of different segments being independently energizable.

A medical treatment method in accordance with the present invention utilizes an ultrasonic medical probe having a plurality of wave-generating elements each for focusing ultrasonic pressure waves at a respective locus of focal points extending in at least one dimension, the loci of focal points being different and spaced from each other. The method comprises (1) placing the probe into effective wave-transmitting contact with one patient, (2) thereafter energizing a first set of the wave-generating elements on the probe to generate ultrasonic pressure waves focused along a preselected first locus extending along at least one dimension inside the patient, (3) subsequently placing the probe into effective wave-transmitting contact with another patient, and (4) thereafter energizing a second set of wave-generating elements on the probe to generate ultrasonic pressure waves focused along a second preselected locus extending along at least one dimension inside the other patient, the second locus being in a different location than the first locus with respect to the probe.

DEFINITIONS

The term "locus" is used herein to denote a set of spatial points, preferably located in a continuous array such as a line.

The term "longitudinal axis" is used herein to denote a line along which a contour or curve is moved to generate a surface in three-dimensional space. Thus, a longitudinal axis of a cylinder may be the axis of symmetry of the cylinder or any line parallel thereto, the cylinder being mathematically generated by translating a circle or a circular segment parallel to the longitudinal axes. A preferred form of an ultrasonic treatment device as described herein includes a wave-generating surface defined by moving a parabola parallel to a longitudinal axis.

The term "wave-generating surface" as used herein designates a surface that is in effective engagement with an electromechanical or electro-acoustic transducer element such as a piezoelectric crystal, whereby an excitation of the transducer element at an ultrasonic frequency causes the surface to vibrate at the same frequency. When the wave-generating surface is placed in wave-transmitting contact with a patient, the ultrasonic vibrations of the surface induce the formation of ultrasonic waves of the same frequency in the patient's tissues.

The word "transverse" as used herein refers to a plane that is perpendicular to, or substantially perpendicular to, a longitudinal axis of an ultrasonic probe. A "transverse cross-sectional shape" is taken in such a plane. A "transverse direction" is a vector in such plane.

The term "transducer element" is used herein to denote a vibrating portion of an ultrasonic probe. A transducer element typically includes a piezoelectric crystal section and at least one pair of electrodes on opposite sides of the crystal section. Thus, a transducer element may be a single monolithic crystal with a predetermined shape and provided with a plurality of electrode pairs in a spaced array. In such a case, the electrode elements by themselves may be viewed as transducer elements disposed along the larger body of the monolithic crystal. Alternatively, where an ultrasonic probe as described herein comprises a plurality of individual crystals, either contiguous with one another or separated by spacer elements, a transducer element may take the form of a single crystal which is typically, but not necessarily, provided with a single pair of energizing electrodes.

DETAILED DESCRIPTION OF THE INVENTION

Figure 1:
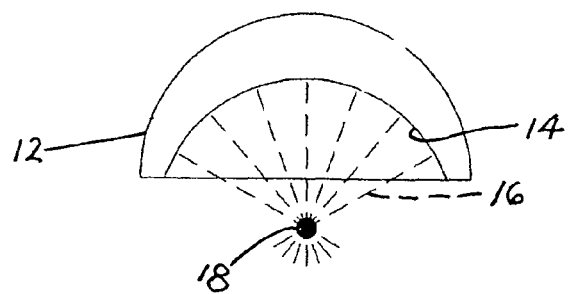
FIG. 1 is a schematic cross-sectional view of a conventional high-intensity focused ultrasound probe.

In the prior art, an ultrasonic medical treatment device has an electromechanical or electro-acoustic transducer element 10 generally in the form of a hemispherical, conical, or parabolic segment, as illustrated in FIG. 1. Energization of the transducer element 10 at ultrasonic frequencies vibrates a hemispherical, conical, or parabolic wave-generating surface 14 to thereby generate ultrasonic waves 16 in a patient's tissues. The waves 16 converge at a focal region 18 as discussed above.

Figure 2:
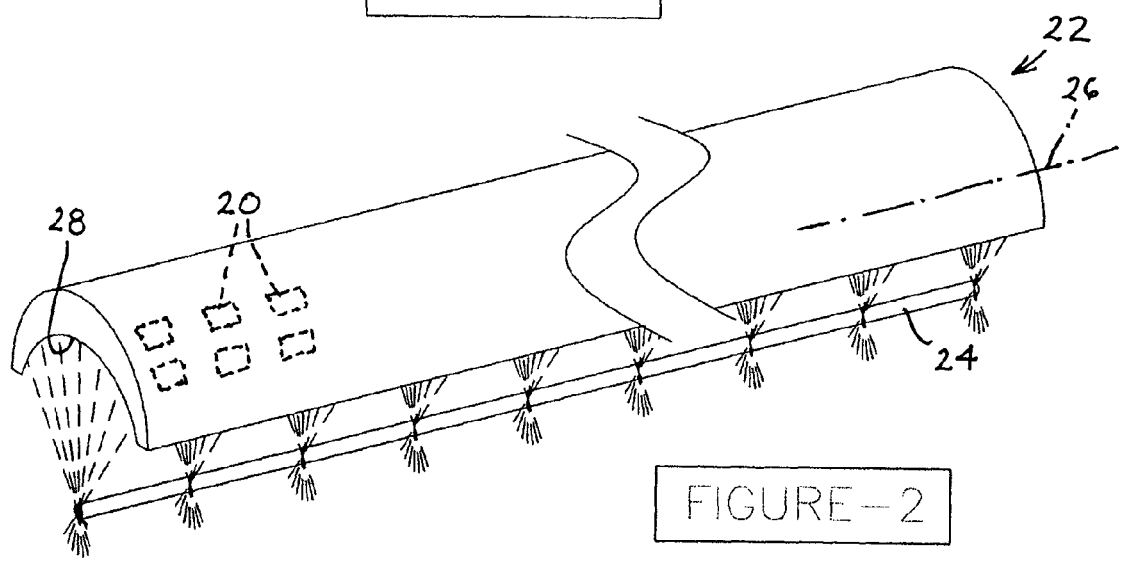
FIG. 2 is a schematic perspective view of a high-intensity focused ultrasound probe in accordance with the present invention.

In the various embodiments of an improved high-intensity focused ultrasound (HIFU) device disclosed herein, the transducer active elements are not segments of a sphere, cone, or paraboloid of revolution 14, or disposed along a spherical, conical, or parabolic section, as in FIG. 1. Instead, as shown in FIG. 2, a probe 22 is in the form of a cylindrical section. The cylindrical section 22 may include a unitary or monolithic element such as a single piezoelectric crystal provided with an array of spaced electrode pairs 20 (FIG. 2). One member of each electrode pair 20 is typically placed along an inner surface of the crystal while the other member is placed along an outer surface of the crystal. By being separately energizable, the electrode pairs 20 effectively divide the monolithic piezoelectric crystal into a plurality of separate transducer segments. Alternatively, the cylindrical section 22 may contain a plurality of individual electro-acoustic transducers (not separately shown in FIG. 2) in the form of separate piezoelectric crystals provided with respective electrode pairs 20. Probe 22 including the crystalline portions thereof and electrodes 20 may be embedded in or in contact with an epoxy lens, as discussed below with reference to FIG. 10. In any event, a focal zone 24 generated by probe 22 is an elongated locus of points having a longer extent in the X dimension than in the Y dimension. Focal zone 24 extends parallel to a longitudinal axis 26 of a generally cylindrical wave-generating surface 28.

Surface 28 has a cross-section, taken transversely or perpendicularly to axis 26, which is a circular, conical or parabolic segment. Focal zone 24 extends along a line or linear locus in space, rather than being confined to a small sphere or rice grain such as focal region 18 (FIG. 1). By sizing the probe 22 and its transducer segments properly, the focal line or locus can be of any desired length.

Figure 3:
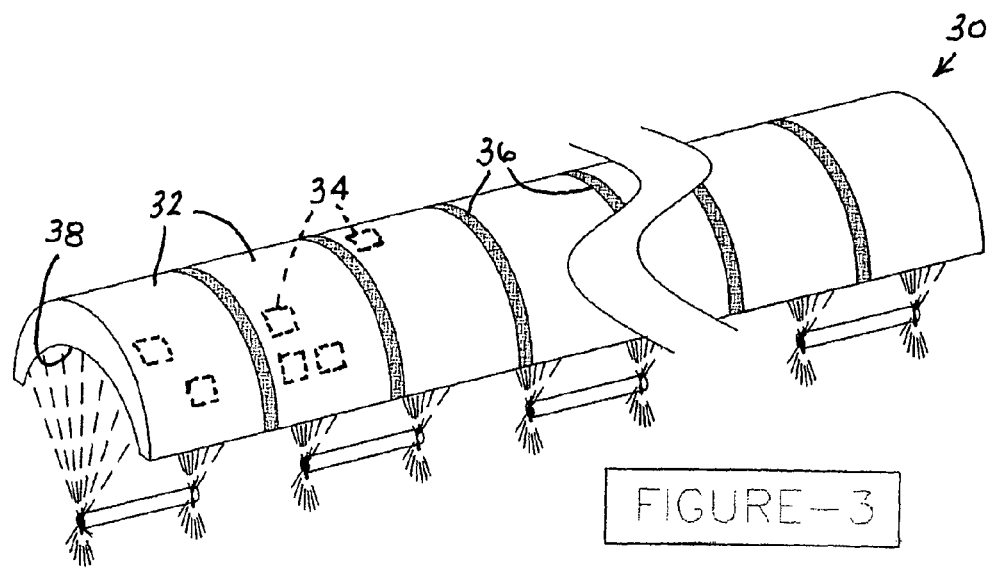
FIG. 3 is a schematic perspective view of another high-intensity focused ultrasound probe in accordance with the present invention.
Figure 4A:
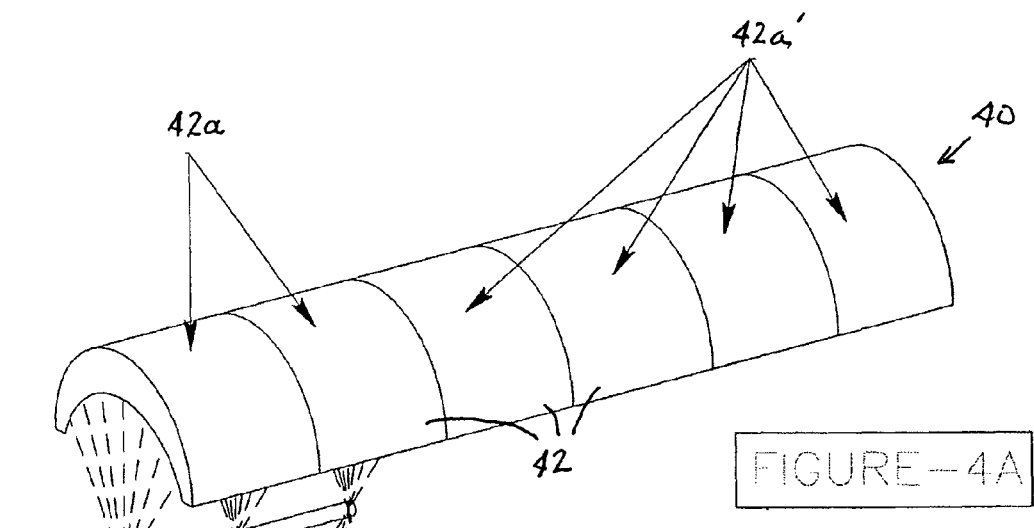
FIG. 4A is a schematic perspective view of a high-intensity focused ultrasound probe in accordance with the present invention, showing a first mode of operation of the probe.
Figure 4B:
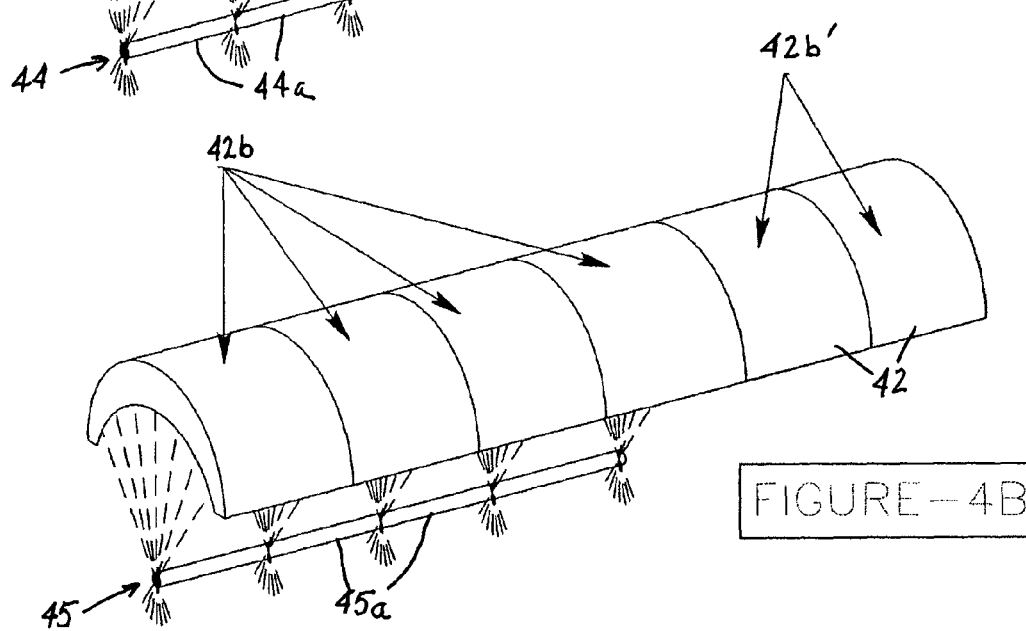
FIG. 4B is a schematic perspective view similar to FIG. 4A, showing a second mode of operation of the probe of FIG. 4A.
Figure 4C:
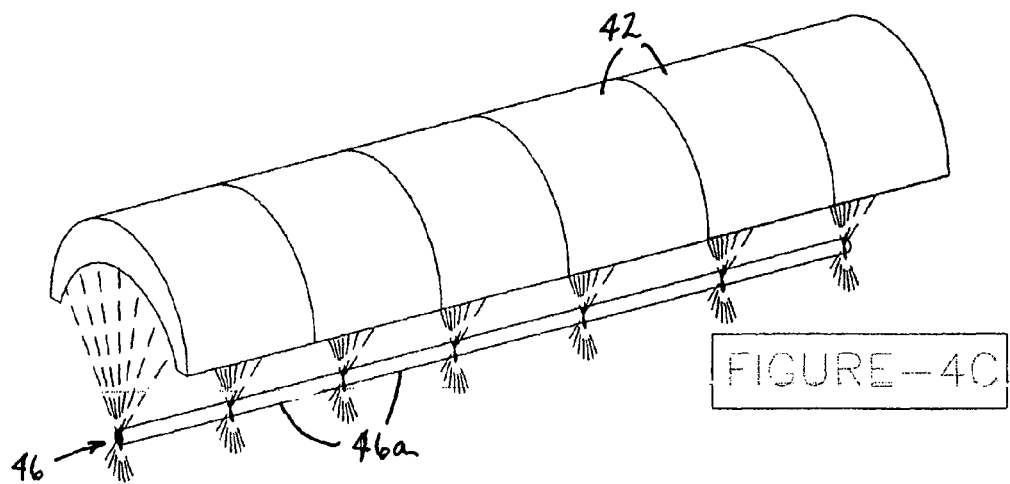
FIG. 4C is a schematic perspective view similar to FIGS. 4A and 4B, showing a third mode of operation of the probe of FIG. 4A.

In the embodiment of FIG. 2, the focal zone 24 has a fixed length and a fixed distance from probe 22. In some cases, the user might wish to vary the length of the focal zone, as well as the distance (range) from the probe. To that end, a probe 30 comprises a plurality of substantially cylindrical segments 32, as illustrated in FIG. 3, each of which may be energized independently of the other probe segments, to focus ultrasonic waveform energy along respective focal loci 38. Probe segments 32 may be shaped piezoelectric transducer crystals. Alternatively, probe segments 32 may take the form of polymeric bodies that contain or incorporate transducer elements 34. In either case, the respective probe segments 32 may be alternately energized and de-energized by methods known to the art. In this way, focal lines of various lengths (up to the maximum length of probe 30) may be created (FIGS. 4A, 4B and 4C). Adjacent probe segments 32 are separated or vibrationally insulated from one another via resilient spacer elements 36. Probe segments 32 have respective concave wave-generating surfaces 38 that are generally contiguous with one another to effectively form a single cylindrical, conical or parabolic wave generating surface when all of the transducer elements 34 are activated.

FIGS. 4A, 4B and 4C show a probe 40 having a plurality of substantially cylindrical wave-generating segments 42 disposed in a linear array. Segments 42 are, or are provided with, piezoelectric ultrasonic transducer elements (not separately illustrated). Segments 42 are preferably spaced by resilient spacer elements (not shown; see spacer elements 36 of FIG. 3) so that the segments 42 are independently activatable to generate focal lines 44, 45, 46 of different lengths.

In FIG. 4A, two adjacent probe segments 42a are activated to generate two collinear focal loci 44a together forming focal line 44. The remaining segments 42a' are deactivated.

In FIG. 4AB, four adjacent probe segments 42b are activated to generate four collinear focal loci 45a together forming focal line 45. The remaining segments 42b' are not activated.

In FIG. 4AC, all probe segments 42 are activated to generate collinear focal loci 46a together forming focal line 46.

Figure 5:
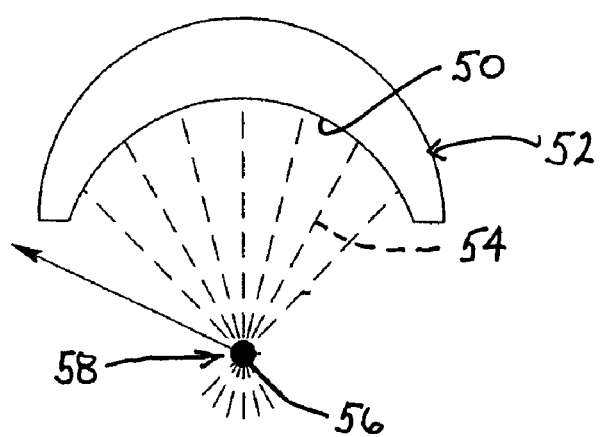
FIG. 5 is a schematic cross-sectional view of a high-intensity focused ultrasound probe in accordance with the present invention.

In all of the present medical device embodiments discussed above, shown generically in FIG. 5, the concave wave-generating surfaces 50 of the probes 52 are shaped to project all of the acoustic energy 54 to the radial centers 56 of the curves. This focusing provides the acoustic energy increase in the tissue volume which then allows for tissue temperature rise. It also causes the focal zone 58 to be a small line in space.

Figure 6:
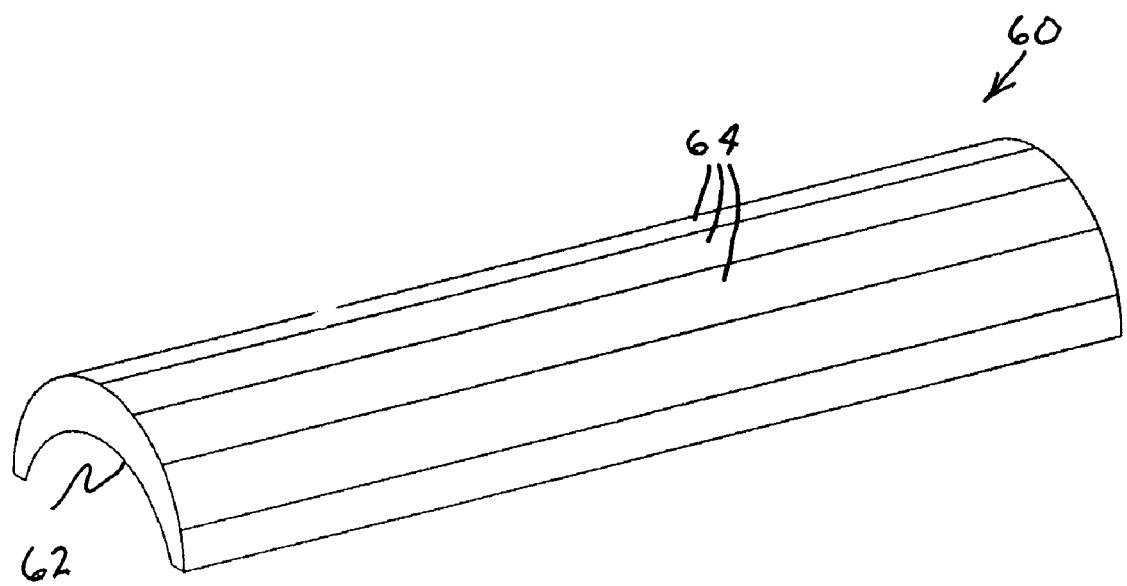
FIG. 6 is a schematic perspective view of a further high-intensity focused ultrasound probe in accordance with the present invention.
Figure 7:
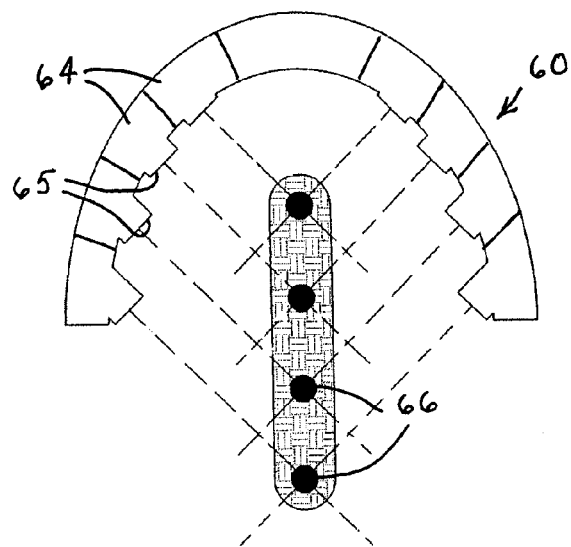
FIG. 7 is a schematic transverse cross-sectional view of the probe of FIG. 6.
Figure 8:
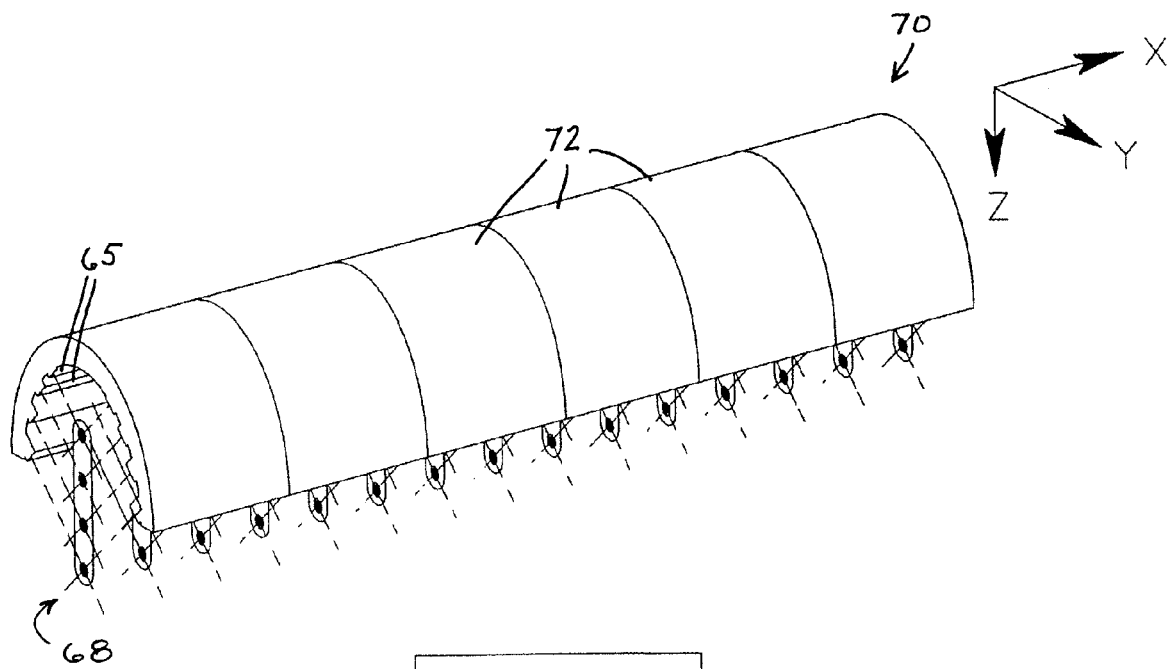
FIG. 8 is a schematic perspective view of a probe similar to that shown in FIGS. 6 and 7, in accordance with the present invention, having the cross-sectional configuration depicted in FIG. 7.

As illustrated in FIG. 6, an ultrasonic probe 60 may have a transducer face 62 that is segmented in the Y direction. Segments 64 have wave-generating surfaces 65 that are stepped and angled relative to one another, as depicted in FIG. 7, so that the focal zone 66 for each segment 64 is displaced in the Z direction, transversely to a longitudinal axis 66 of the probe 60, relative to the segments on either side. The stepped and mutually angled configuration of surfaces 65 causes the focal point or zone 66 of any given element or segment 64 to be above or below the adjacent segments. In this way, as shown in FIG. 8, a composite focal zone 68 with significant dimension or extent in the X and Z planes may be created. FIG. 8 more particularly shows a probe 70 including a linear array of wave-generating segments 72 contiguous with and connected to each other. Each segment 72 in turn comprises a plurality of stepped and angled wave-generating surfaces 65 as described above with reference to FIGS. 6 and 7.

Figure 9:
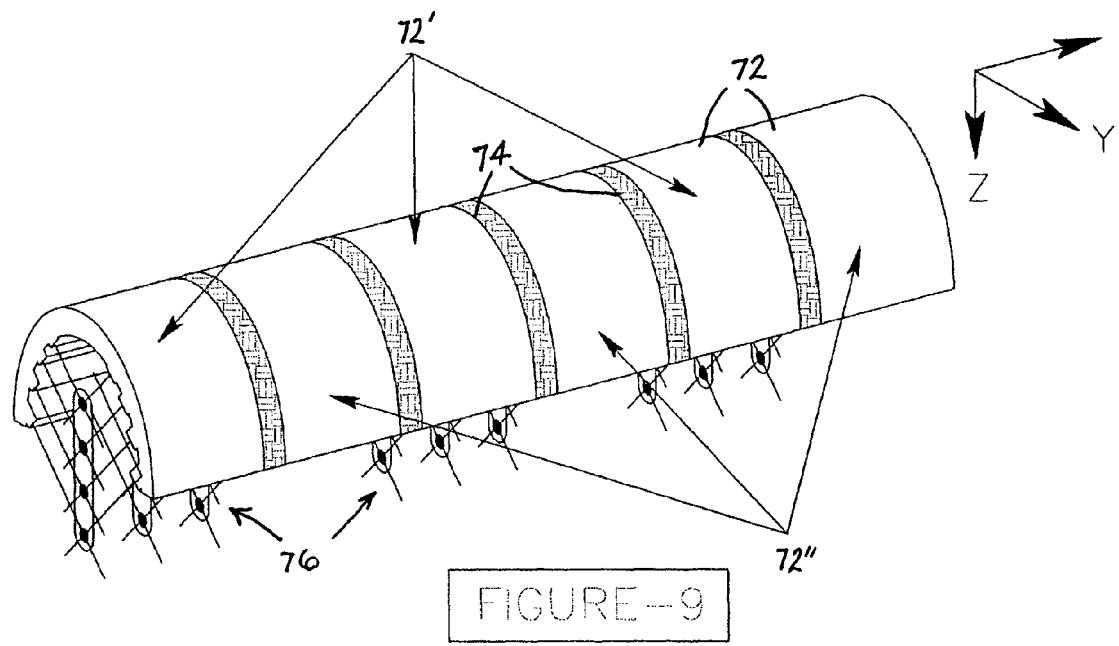
FIG. 9 is a schematic cross-sectional view of yet another high-intensity focused ultrasound probe in accordance with the present invention, representing a modification of the probes shown in FIGS. 6-8.

As depicted in FIG. 9, segments 72 may be separated by resilient spacer elements 74 to enable a selective energization of the segments 72. For instance, as depicted in FIG. 9, selected segments 72' may be energized while segments 72" are de-energized, thereby generating several discontinuous focal zones 76. If the activating energy is maintained for a sufficient period of time, the volume of each zone 76 will expand until the zones connect into a solid oblong cross section.

The electronics for turning these segments on and off, as well as the electronics for creating the ultrasonic acoustic energy are well known and are outside the scope of the present disclosure.

The wave-generating function of the probes discussed hereinabove is attained by transducer elements in the form of piezoelectric crystals. Such crystals are commonly used in the industry since they are efficient transformers of electrical into mechanical energy. These crystals are molded into the shapes desired and segmented as known in the prior art. The back sides of the crystals have electrodes (not shown) placed above the areas which are desired to be active.

Figure 10:
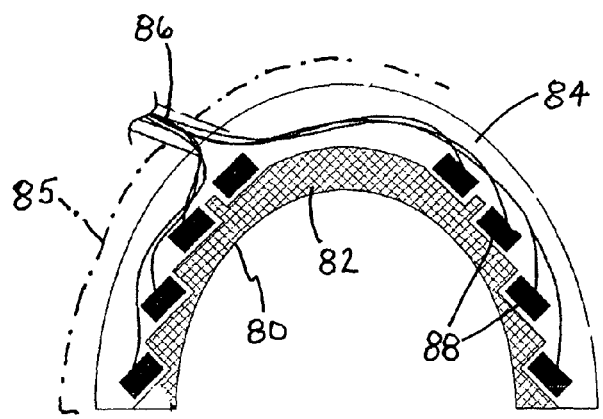
FIG. 10 is a schematic cross-sectional view of a high-intensity focused ultrasound probe such as that of FIGS. 6-9, showing structural details in accordance with the present invention.

As depicted in FIG. 10, the wave-generating surface 78 of a probe segment 80 as discussed above may be formed by an acoustic lens 82, usually made from poured epoxy resin. The shape and thickness of the lens may be varied to achieve a desired performance.

As further depicted in FIG. 10, the backing 84 of the probe or transducer segment 80 is a metal stamping or shaping which will give the elements of the transducer segment the desired focal direction(s). This backing 84 can be made of a heavy metal such as tungsten, or an epoxy pouring. A casing (not shown) is placed over the entire assembly to protect the assembly and to provide a hand hold for the operator. When a cable bundle 86 is attached to an electronic generator, the system may be turned on and used in much the same way as conventional ultrasonic systems.

FIG. 10 depicts transducer elements 88 in the form of separate piezoelectric crystals embedded in backing 84. As discussed above, individual probe segments may be molded or shaped piezoelectric crystals that are provided with electrodes connected to cable bundle 86.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An ultrasonic medical treatment device comprising:
a probe having a plurality of wave-generating elements each for focusing ultrasonic pressure waves at a respective linear locus of focal points extending in at least one dimension, the loci of focal points being different and spaced from each other, said wave-generating elements being translationally and rotationally stationary relative to one another,
said wave-generating elements including ultrasonic electromechanical transducer elements for vibrating at least one surface to generate ultrasonic pressure waves focused along the respective loci, said wave generating elements having wave-generating surfaces of different fixed geometric shapes configured to focus ultrasonic waves along the respective loci and having longitudinal axes parallel to and spaced from the respective wave generating-surfaces, the loci of focal points of the different wave-generating surfaces being parallel to the respective longitudinal axes,
said transducer elements of different ones of said wave-generating elements being independently energizable to focus ultrasonic waveform energy selectively along said different loci.

2. The medical treatment device defined in claim 1 wherein said probe is elongate and has a longitudinal axis and wherein said loci are linear and extend parallel to said longitudinal axis.

3. The medical treatment device defined in claim 2 wherein said probe has an elongate wave-generating concave surface formed along said longitudinal axis.

4. The medical treatment device defined in claim 3 wherein said probe includes a plurality of segments each having a respective wave-generating concave surface, said ultrasonic electromechanical transducer elements vibrating the respective wave-generating concave surfaces to generate ultrasonic pressure waves focused along respective linear loci extending parallel to said longitudinal axis.

5. The medical treatment device defined in claim 4 wherein adjacent ones of said segments are joined to and vibrationally isolated from one another by resilient spacer elements, different ones of said segments being independently energizable.

6. The medical treatment device defined in claim 4 wherein said loci are parallel to and spaced from one another, said segments being spaced from one another in a direction transverse to said longitudinal axis.

7. The medical treatment device defined in claim 6 wherein said probe has a plane of symmetry, said segments including pairs of segments, each such pair including members disposed on opposite sides of said plane.

8. The medical treatment device defined in claim 7 wherein said probe includes an epoxy lens along an inner side and a backing along an outer side, said transducer elements being disposed between said epoxy lens and said backing.

9. The medical treatment device defined in claim 8 wherein said transducer elements are disposed in a stepped array.

10. The medical treatment device defined in claim 1 wherein said probe includes a plurality of segments disposed in an arc relative to one another, each of said segments having a respective wave-generating surface, said ultrasonic electromechanical transducer elements vibrating the respective wave-generating surfaces to generate ultrasonic pressure waves focused along respective linear loci extending parallel to said longitudinal axis and transversely spaced from one another.

11. The medical treatment device defined in claim 10 wherein said probe has a plane of symmetry, said segments including pairs of segments, each such pair including members disposed on opposite sides of said plane.

12. The medical treatment device defined in claim 1 wherein said probe includes an epoxy lens along an inner side and a backing along an outer side, said transducer elements being disposed between said epoxy lens and said backing.

13. The medical treatment device defined in claim 1 wherein said transducer elements are disposed in a stepped array.

14. The medical treatment device defined in claim 1 wherein groups or sets of said transducer elements are independently energizable.

15. The medical treatment device defined in claim 1 wherein said probe includes a plurality of segments each having a respective wave-generating concave surface, adjacent ones of said segments being joined to one another by resilient spacer elements, different ones of said segments being independently energizable.

16. The medical treatment device defined in claim 1 wherein said probe includes a plurality of segments each having a respective wave-generating concave surface, said ultrasonic electromechanical transducer elements vibrating the respective wave-generating concave surfaces to generate ultrasonic pressure waves focused along respective linear loci extending parallel to said longitudinal axis.

* * * * *